US005353930A

United States Patent [19]

Berry, Jr.

[11] Patent Number: 5,353,930
[45] Date of Patent: Oct. 11, 1994

[54] VACUUM-FORMED ENCLOSURE WITH VACUUM-FORMED APERTURES

[75] Inventor: Bernie B. Berry, Jr., Indianapolis, Ind.

[73] Assignee: Carr Metal Products, Inc., Indianapolis, Ind.

[21] Appl. No.: 102,720

[22] Filed: Aug. 6, 1993

[51] Int. Cl.⁵ .......................................... B65D 81/18
[52] U.S. Cl. ...................... 206/370; 206/439; 206/557; 264/154; 264/536; 264/553
[58] Field of Search .............. 206/439, 370, 369, 562, 206/563, 564, 557; 264/544, 553, 154, 536; 422/297, 300, 301, 302, 303, 304

[56] References Cited

U.S. PATENT DOCUMENTS

| | | | |
|---|---|---|---|
| 3,955,672 | 5/1976 | Brundage | 206/562 |
| 4,191,291 | 3/1980 | Brown. | |
| 4,798,292 | 1/1989 | Hauze. | |
| 4,844,852 | 7/1989 | Keyses et al. | 264/544 X |
| 5,098,676 | 3/1992 | Brooks, Jr. | |
| 5,108,530 | 4/1992 | Niebling, Jr. et al. | 264/544 X |
| 5,165,539 | 11/1992 | Weber et al. | 206/370 X |

Primary Examiner—Jacob K. Ackun, Jr.
Attorney, Agent, or Firm—Woodard, Emhardt, Naughton, Moriarty & McNett

[57] ABSTRACT

A vacuum-formed storage tray for autoclaving medical and dental instruments includes a base panel surrounded by a plurality of integrally joined sidewalls so as to create an interior storage area. The base panel defines a plurality of sterilant apertures. The base panel and sidewalls are created by a vacuum-forming operation which concurrently creates by vacuum forming a plurality of aperture bosses. The vacuum-formed aperture bosses are closed as formed and must be subjected to a post-forming machining operation to cut off the closed end of each aperture boss. Once the closed ends are cut off, the closed aperture bosses become open sterilant apertures. The creation of a plurality of sterilant apertures by a vacuum-forming operation can replace any drilling operations for sterilant holes and economically allows greater variety as to the style and shape of apertures which can be formed in the base panel of the storage tray.

4 Claims, 3 Drawing Sheets

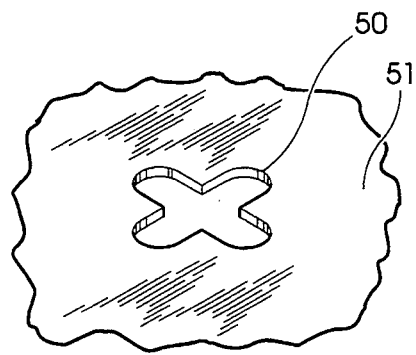
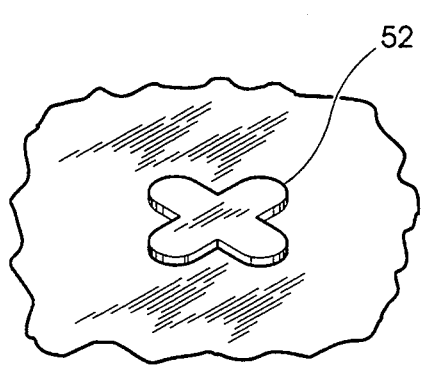
Fig. 5    Fig. 5A
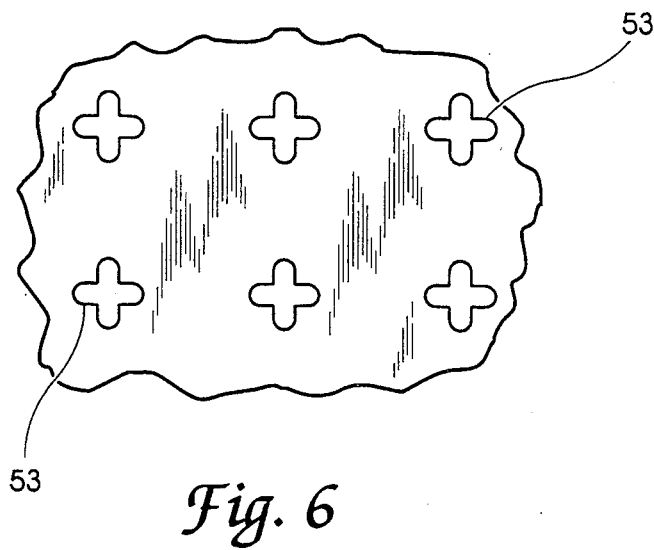
Fig. 6
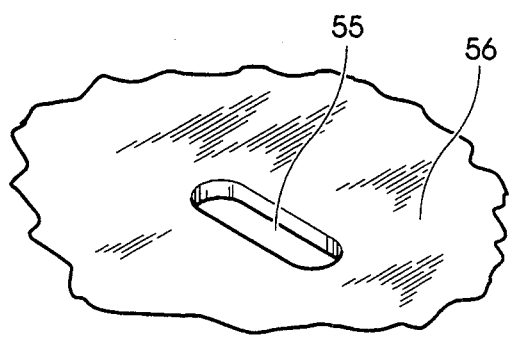
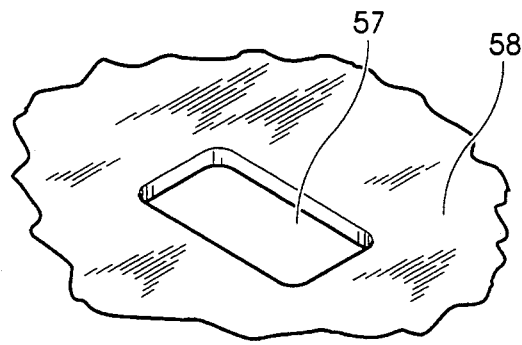
Fig. 6A    Fig. 6B

VACUUM-FORMED ENCLOSURE WITH VACUUM-FORMED APERTURES

BACKGROUND OF THE INVENTION

The present invention relates in general to plastic autoclave enclosures which are used for the receipt and storage of medical and dental devices and equipment. More particularly the present invention relates to the manufacture of plastic autoclave enclosures where the enclosure as well as the flow through apertures for sterilant are fabricated in part by vacuum forming.

In the design of autoclave cassettes and enclosures there are a number of options for suitable materials. While high temperature resistance is obviously one important property of the selected material, there are other material properties of importance. The machineability or shapeability of the material is a factor as are weight, strength and durability. Questions about the handling ease and availability of the material as well as how the material will stand up after years of use, may need to be answered.

Currently most autoclave cassettes and enclosures are fabricated out of metal (aluminum or stainless steel) or plastic using some high temperature thermosetting or thermoforming material which can be injection molded or vacuum formed. Plastic autoclave enclosures offer advantages in weight reduction and to some extent greater shaping and styling freedom. Plastic autoclave enclosures generally offer a shorter delivery time than metal enclosures and may have a lower cost. Possible drawbacks of plastic as compared to metal include strength, rigidity and durability.

Another concern with plastic autoclave enclosures is the ability to provide a large number of steam or sterilant apertures without either weakening the enclosure or incurring an unacceptable manufacturing cost as the sterilant apertures are typically drilled holes. When the sterilant apertures are drilled holes there is a drilling operation which must be set up and performed after the plastic enclosure is molded or formed. High temperature plastics require a careful drilling operation which is time consuming. With straight drilled holes the panel of plastic material into which the holes are drilled is weakened and thus there is a practical limitation as to the number and size of holes which can be drilled per unit area.

A variety of plastic autoclave enclosures are known to exist and the following patent listing is believed to provide a representative sampling of earlier plastic enclosures:

| U.S. Pat. No. | Patentee   | Issue Date     |
|---------------|------------|----------------|
| 5,098,676     | Brooks, Jr.| March 24, 1992 |
| 4,191,291     | Brown      | March 4, 1980  |
| 4,798,292     | Hauze      | Jan. 17, 1989  |

In the present invention the plastic autoclave enclosure is created by vacuum forming and the steam or sterilant apertures are created as part of the vacuum-forming step that creates the enclosure. What is initially created by the vacuum-forming operation are closed bosses which are then machined to create apertures. In looking at the tray portion of the enclosure these aperture bosses are recessed (concave) relative to the interior and extend below the bottom surface of the base panel of the enclosure tray portion. If the aperture bosses are formed in the lid portion of the enclosure then they are recessed relative to the exterior and extend inwardly into the interior of the enclosure. Since these bosses are closed there are no open apertures created immediately after the vacuum-forming operation. However, a post-forming milling or planing operation cuts off the closed end of each aperture boss thereby opening up each boss into a cleanly formed aperture. In one embodiment a mechanical assist is provided by the male side of the vacuum-forming die in order to create tighter corners and radii for the aperture bosses. In another embodiment a pressure box is used and air pressure is introduced into a sealed chamber over the softened plastic. This allows the part to be formed with much greater definition and detail.

A related benefit of the present invention and of the mechanical assist or pressure box as contrasted to straight drilled holes is the ability to create virtually any size and shape or style of sterilant aperture. Specialized aperture shapes may be used to stylize a case in order to create an appearance that denotes a certain manufacturer's product. A further benefit afforded by the present invention is to create a higher percentage of open area and thus a greater capacity for passage of sterilant, and a faster (shorter) sterilizing time cycle.

SUMMARY OF THE INVENTION

A vacuum-formed storage tray for receiving articles to be autoclaved according to one embodiment of the present invention comprises a base panel having a plurality of vacuum-formed apertures and a plurality of sidewalls integrally formed with the base panel and defining an interior storage area.

A method for creating a vacuum-formed storage tray with a plurality of sterilant apertures according to a related embodiment of the present invention comprises the steps of first providing a vacuum-forming die having a plurality of aperture recesses, placing a preheated sheet of plastic to be vacuum formed onto the heated vacuum-forming male die, drawing a vacuum on the underside of the sheet of plastic permitting atmospheric pressure to push it into and against the forming die and into the aperture recesses so as to create a plurality of aperture bosses in the sheet of plastic wherein each boss has a raised closed end, and then machining off the closed end of a plurality of the aperture bosses in order to open those closed bosses and thereby create a plurality of sterilant apertures.

One object of the present invention is to provide an improved vacuum-formed storage tray with vacuum-formed sterilant apertures.

Related objects and advantages of the present invention will be apparent from the following description.

BRIEF DESCRIPTION OF THE DRAWINGS

FIG. 5 is a perspective view of one female die portion for a specially styled sterilant aperture.

FIG. 5A is the male die portion which corresponds to the FIG. 5 female die portion according to the present invention.

FIG. 6 is a partial top plan view of a storage tray base panel as configured with sterilant apertures created according to the FIGS. 5 and 5A die portions.

FIG. 6A is a partial perspective view of an alternative sterilant aperture shape which may be created according to the present invention.

FIG. 6B is a partial perspective view of an alternative sterilant aperture shape which may be created according to the present invention.

DESCRIPTION OF THE PREFERRED EMBODIMENT

Figure 1:
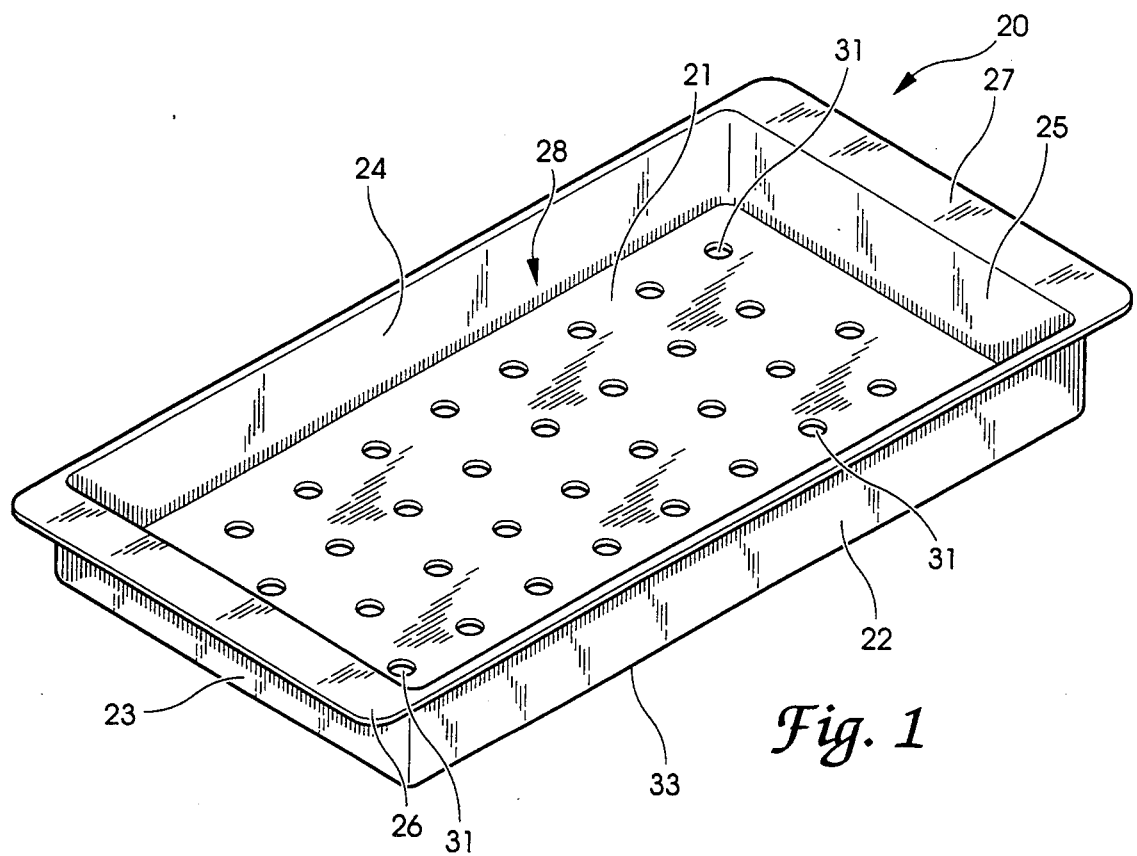
FIG. 1 is a perspective view of a vacuum-formed autoclavable storage tray including vacuum-formed sterilant apertures according to a typical embodiment of the present invention.

For the purposes of promoting an understanding of the principles of tile invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring to FIG. 1 there is illustrated a plastic storage tray 20 which includes a substantially flat base panel 21, four sidewalls 22-25 and end flanges 26 and 27. In the preferred embodiment the entire storage tray is formed as a single, integral unit by means of a vacuum-forming operation. The four sidewalls 22-25 in combination with base panel 21 define an interior storage area 28. The sheet of plastic material used for storage tray 20 is first softened by heating and then pulled over or into a heated die by the application of a high force vacuum. The vacuum-formed storage tray has smoothly rounded interior and exterior corners and can be trimmed to yield smooth and clean peripheral edges throughout.

By the application of an enclosing lid which may either latch to storage tray 20 or could be hinged to the storage tray 20 a plastic autoclave enclosure is created. Although a variety of enclosing techniques and lid designs are suitable and available for use with the storage tray 20, the focus of the present invention is on tile vacuum forming of sterilant apertures in a panel of plastic, as illustrated in base panel 21.

There are two types of plastics most commonly used to produce autoclave trays, cases and enclosures. Either of these two types of plastics would be regarded as suitable for the present invention. One plastic material is polyphenylsulfone which is produced exclusively by Amoco Performance Products, Inc. and marketed under the trade name of "Radel R" The other suitable plastic for the present invention is polyetherimide which is produced exclusively by GE Plastics and marketed under the trade name of "Ultem". Either of these two plastics are good choices for the present invention because they have high heat distortion temperatures, good chemical resistance, good impact strength and are thermoformable. As between the two plastics, "Radel R" may be the preferred choice as it has a higher impact strength than does "Ultem".

With regard to the specifics of the vacuum-forming operation, the present invention discloses a specific approach and a specific style of molding die as well as a post forming machining operation. However, the general concepts, principles and structure of vacuum-forming are believed to be well-known. The basic process involves a pressure forming machine which is commercially available. To this somewhat standard piece of equipment a specifically styled mold is provided and a sheet of thermoformable plastic. The entire operation may be automated with appropriate sensors and controllers so as to maintain proper times and temperatures. The sheet of plastic is placed into a pressure former where it is held horizontally by a series of clamp frames. The pressure former then moves the plastic sheet into an oven where the plastic is heated to a predetermined temperature so as to soften the plastic and make it formable. When the plastic is at the proper temperature for the particular plastic which has been selected, it is moved into the forming area. At this point the softened plastic comes into contact with the selected mold and a seal is formed around the perimeter edges of the mold. A vacuum is then applied through the mold and because of the seal and in cooperation with atmospheric pressure pulls the plastic into the mold causing the plastic to take the shape of the mold. The mold is heated in order to help maintain the thermoforming character of the plastic and allow it to more accurately conform to the shape of the mold.

As detailed hereinafter, a mechanical assist may be used so as to force the softened plastic into each of the corners and crevices of the mold in order to create greater detail and definition to the plastic part. In lieu of a mechanical assist, a pressure box may be used on top of the softened plastic so as to introduce a higher air pressure above the plastic thereby pushing it into the hollow shapes of the mold.

Figure 2:
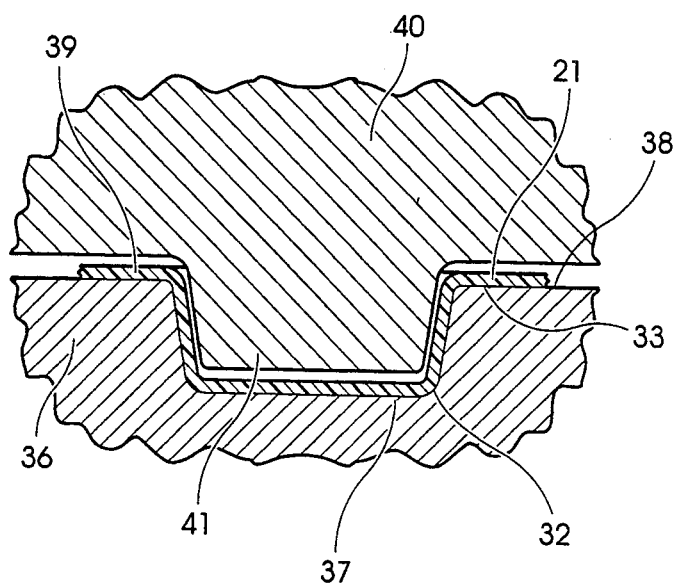
FIG. 2 is a partial, side elevational view in full section of the vacuum-forming die arrangement with a sheet of plastic loaded therein which is used to create the FIG. 1 storage tray.

Base panel 21 defines a plurality of sterilant apertures 31 which are initially formed as a raised and closed boss by the same vacuum-forming operation which creates storage tray 20. The actual aperture bosses 32 which are created are recessed from the interior of storage tray 20 so as to extend from the interior top surface of panel 21, through panel 21 and outwardly beyond the bottom surface 33 of base panel 21. The specific male-female die arrangement used to create each raised (or outwardly extending) and closed boss which is the starting point for the corresponding aperture 31 is illustrated in FIG. 2. Once the boss 32 is created by the vacuum-forming operation a post-forming machining operation cuts the raised boss 32 to a predetermined height relative to the bottom surface 33 of panel 21 (see FIG. 3). This height may be flush to up to the height of any feet on the tray. What results is a cleanly trimmed aperture 31 (see FIG. 4) which has been created in panel 21 without the need for any drilling operation. The effect of this process is to recreate the original tray strength, depending on the size of the aperture. By repeating the male-female die combination of FIG. 2 into uniform pattern, the aperture pattern of FIG. 1 is created. The machining of tile formed bosses 32 can be accomplished with an end mill on a CNC milling machine, by hand with a hand held router or by a similar machining method. Generally the part would be placed into a holding fixture and held in a generally horizontal position. The cutting blade would then be placed next to the raised bosses 32 and set at the desired height. The rotating cutter would then move horizontally across the bottom surface of the base panel 21 (now directed as the upper surface) cutting through each boss and cutting off the closed end of each boss thereby creating an open aperture for the flow through of sterilant.

Referring more specifically to FIG. 2, die 36 is the female portion of the die combination and provides a recessed pocket 37 for each desired aperture 31. The depth of pocket 37 equates to the height of boss 32 and die surface 38 coincides with the bottom surface 33 of base panel 21. The designed size clearance between the male and female die portions equates to the thickness of plastic to be formed into the raised boss. In FIG. 2 a heated sheet 39 of plastic is placed over heated die 36 and a vacuum is drawn. The application of this vacuum pulls the warmed, shapeable sheet of plastic against heated die 36 and draws the plastic into any recesses, pockets or other relief formed in die 36. The use of a heated die (i.e., die 36) keeps the plastic from being quickly chilled and this reduces the chances of the plastic cracking or crazing. By keeping heated die 36 at approximately 500° F. any thermal stresses in the plastic are minimized.

In order to force the plastic into the corners of recesses such as pocket 37 and to ensure that the shape of boss 32 closely matches pocket 37 a mechanical assist is provided by means of male die 40. Male die 40 includes a boss portion 41 which is precisely shaped and sized to push the sheet 39 of softened plastic into all areas and corners of pocket 37. The end result is a precisely and uniformly shaped boss 32 as is illustrated in FIG. 3.

Figure 2A:
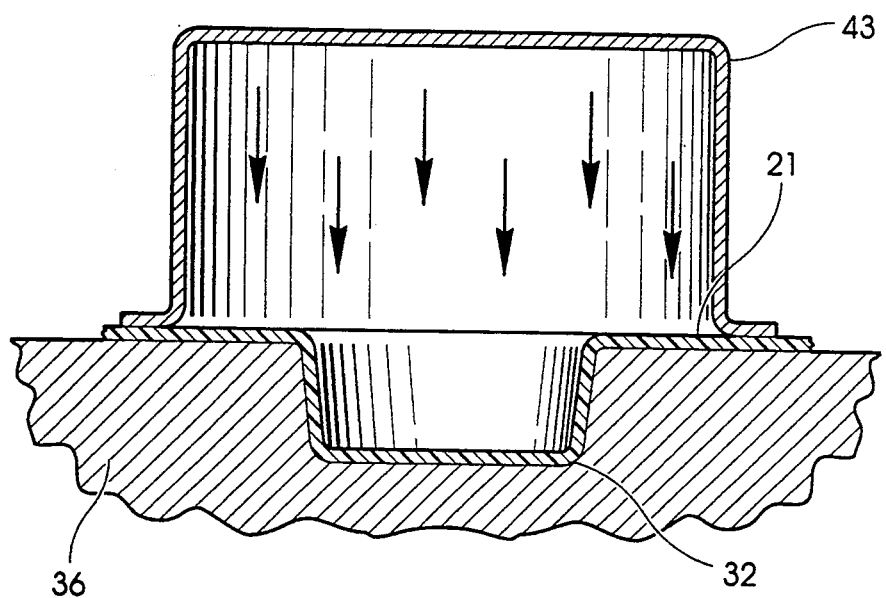
FIG. 2A is a diagrammatic, partial side elevational view in full section of an alternative vacuum-forming die arrangement according to the present invention.

In lieu of the mechanical assist which is provided by means of male die 40 as illustrated in FIG. 2, a pressure box 43 as is illustrated in FIG. 2A may be used. The lower portion of FIG. 2A is virtually identical to the lower portion of FIG. 2 and tile only difference between the two is that male die 40 has been removed and replaced by pressure box 43. The pressure box is used in the following manner. After the plastic has been heated to the predetermined temperature and has been moved into position over the mold (die 36), the pressure box 43 is moved into position as is illustrated in FIG. 2A. Pressure box 43 is a five-sided box fabricated from aluminum with air-tight welded joints and seams which are capable of withstanding at least 100 psi of air pressure. The sixth side of the box is open and it is this open side which comes down into contact with the top surface of the softened plastic sheet. In effect, the plastic sheet is sandwiched between die 36 on its underside and pressure box 43 on its top side. The open edge of the pressure box 43 comes into contact with the plastic sheet and actually forms a tight seal around the outside edges of the plastic so as to create a sealed chamber. Air pressure is then introduced into this sealed chamber and this air pressure pushes the softened plastic against the mold (die 36) with a much greater force than what could be achieved by simply drawing a vacuum through die 36 from the underside. This greater air pressure pushing on the top surface of the softened plastic causes the plastic to flow and conform more precisely to all the cavities and corners of die 36 so that the vacuum-formed plastic part which results has a much greater definition and detail. It will also be understood that all of these procedural steps take place within a relatively short time period. Typically a few seconds, so that the plastic does not cool and begin to become rigid. After the plastic part is completely formed it is allowed to cool to a temperature below its heat distortion point at which time the part may then be removed from the machine.

Figure 3:
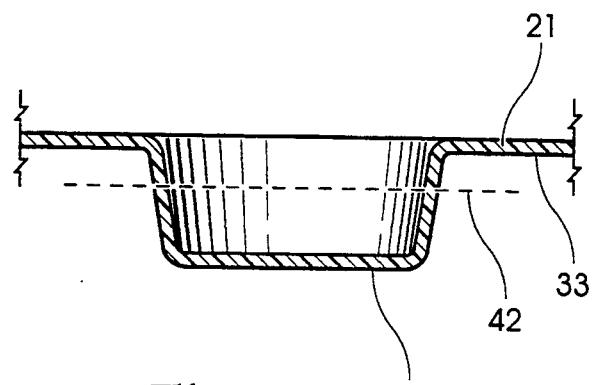
FIG. 3 is a side elevational view in full section of one vacuum-formed sterilant aperture boss according to the present invention.

As illustrated in FIG. 3, it is to be noted that boss 32, regardless of the fabrication method which is selected, extends beyond the bottom surface 33 of base panel 21. In the preferred embodiment each boss 32 has a slightly tapering shape and is completely closed. Each boss 32 can be thought of as being formed by a surrounding aperture wall and an enclosing end. The aperture wall that creates each boss 32 is an extension of the base panel 21 and is connected to the base panel by a curved inner edge.

Figure 4:
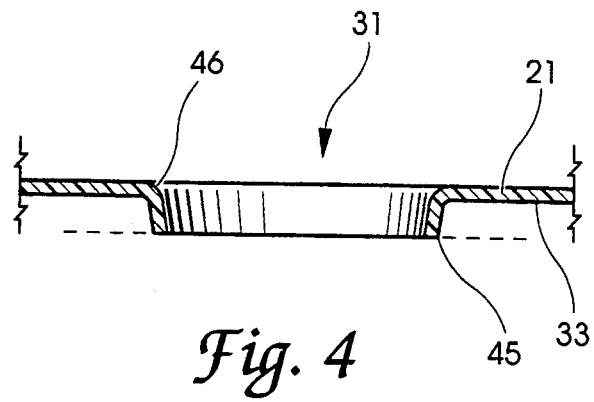
FIG. 4 is a side elevational view in full section of the FIG. 3 aperture boss after a post-forming machining operation performed to create a sterilant aperture according to the present invention.

As there were no openings or other perforations in the beginning sheet of plastic, and no other relief created by the female die, each raised aperture boss 32 is closed and each one has generally the same size, shape and appearance. However, the style of raised aperture boss 32 may be varied and a plurality of different shapes may be incorporated into the same storage tray. While boss 32 can be made in virtually any size and shape and while virtually any number may be provided in any type of spacing or arrangement, in order to open these closed aperture bosses a post-forming operation must occur. This post-forming operation machines off a majority of the raised portion of each boss 32 as would occur with a milling or planing operation along the surface denoted by broken line 42. Depending upon the desired finished style for each aperture 31, the raised aperture bosses may be cut anywhere from flush with the bottom surface 33 to raised as indicated by line 42. The result of this post-forming milling or machining operation which planes off the raised portion of each aperture boss is illustrated in FIG. 4.

In comparing the nature of aperture 31 which results after the raised portion of boss 32 is cut off to a drilled hole there are several differences. Each of these differences is believed to be a very distinct advantage of the vacuum-formed aperture 31 of the present invention over a conventionally drilled hole. One difference (advantage) of the present invention when comparing the differences between a vacuum-formed aperture and a drilled hole relates to the time and cost to perform the operations. The ability to form a shape into plastic offers a considerable time savings over machining that same shape. A formed aperture such as by vacuum-forming has all of its dimensions and location formed in the part by the nature of the dies. Once the dies are created the part conforms time after time without the need to fixture or set up the piece. Although there is a machining operation involved as part of the vacuum-forming process of the present invention, there is very little need for precise accuracy when machining off the closed ends of the various vacuum-formed bosses. The only actual dimension which is controlled is the height of the cutter which ultimately controls the height or extension of the aperture wall beyond the surface of the base panel. Because there is very little need for precise tolerances or accuracy in this machining operation, the speed of tile cutter can be increased as well as its size to shorten the time requirements. When machining an aperture into a part accuracy becomes much more important. A smaller cutter and slower cutting speeds are required and the cutter or drill must be located much more accurately which typically requires holding fixtures and the like. If we are considering a hole or shape other than circular the cutter must first plunge through the plastic before it can begin to cut the desired shape. This is a slow and relatively high risk operation that could result in increased scrap. Further, a machined aperture will require debarring around its edges on both the inside and outside surfaces of tile part. A formed aperture requires deburring only on the outside or back side of the aperture wall because no machining takes place on the inside lip where the aperture wall joins to the base panel. Even with drilling which may be the most popular method of producing sterilant apertures in plastic, deburring on both the inside and outside surfaces of the part is still required.

Another difference (i.e., advantage) is the ability to create virtually any shape for aperture 31 as illustrated in FIG. 6. This allows special patterns and styles to be created and would enable special logos and trademark shapes to be designed into custom autoclave enclosures. Although the "star" pattern illustrated in FIG. 6 has uniform spacing between each aperture, uniform spacing is not a requirement and not limiting to the present invention.

A further difference (advantage) is the small raised lip 45 which may protrude at varying heights beyond bottom surface 33. Although illustrated as slightly raised, this lip can have a greater raised height depending on the cutting plane. The redirection of the plastic so as to extend into and form lip 45 adds strength and rigidity to panel 21 over the weakening of panel 21 caused by drilling holes into the panel. As the raised height of lip 45 increases so does the rigidity of panel 21.

The still further difference (advantage) relates to the inside curved edge 46 which extends around the upper, inner periphery of aperture 31. When the vacuum-formed storage tray 20 is used for medical or dental instruments or any items which are to be autoclaved, there will be a passage through as well as a collection of moisture in the enclosure. By providing a gradually and smoothly curved edge 46 to each aperture 31, the drainage of any moisture or condensation is facilitated. Since the raised lip 45 provides greater rigidity, the size (i.e., area) of each aperture can be enlarged as well as the number of apertures over what can be done with drilled holes. As the total aperture area increases there is a corresponding increase in the flow rate of sterilant through the enclosure.

As mentioned, an example of one of the possible special shapes for the apertures to be formed in storage tray is illustrated in FIG. 6. The FIG. 6 apertures 53 result by vacuum-forming raised bosses which are created in the base panel by the use of the FIG. 5 vacuum-forming female die and the FIG. 5A mechanical assist male die. Referring to FIG. 5, the specially shaped female recess 50 is illustrated as disposed down into die panel 51. The corresponding and matching male portion (boss) 52 (illustrated in FIG. 5A) provides the mechanical assist to precisely shape the plastic into all edges and corners of recess 50. The vacuum forming of raised bosses by the use of a plurality of these male and female die forms followed by the machining operation to cut off the raised, closed end of each aperture boss results in the FIG. 6 aperture pattern. Although only one female recess and one male portion 52 are illustrated in FIGS. 5 and 5A, a plurality of these male and female die forms are arranged in a uniform pattern as would be expected and understood in order to create the aperture pattern in FIG. 6. In FIGS. 6A and 6B other aperture shapes are disclosed which may be created by the present invention. Aperture 55 in base panel 56 is an oblong shape and aperture 57 in base panel 58 is a rectangular shape.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A vacuum-formed storage tray comprising:
    a base panel having an outer surface and opposite thereto an interior surface;
    a plurality of side panel integrally joined with and around said base panel and each of said plurality of side panels extending in a first direction away from said interior surface;
    a plurality of side panel flanges, one each of said plurality of side panel flanges being integrally formed with a corresponding one of said side panels; and
    a plurality of sterilant passageways disposed in said base panel, each passageway of said plurality of sterilant passageways being defined in part by a vacuum-formed sidewall and in part by a radiused edge portion which integrally connects the corresponding vacuum-formed sidewall with said base panel, each sterilant passageway having a first aperture which is generally coincident with the base panel and a second aperture defined by said vacuum-formed sidewall, each vacuum-formed sidewall extending in a second direction away from said outer surface, said second direction being opposite to said first direction and wherein the outermost extent of each of said vacuum-formed sidewalls in said second direction creating a free edge, each free edge defining its corresponding second aperture.

2. A vacuum-formed storage tray with a plurality of sterilant apertures fabricated by the following process steps:
    providing a vacuum-forming die having a plurality of aperture recesses;
    placing a sheet of plastic to be vacuum formed to create said storage tray onto said vacuum-forming die, said sheet of plastic having an interior-to-the-tray surface and opposite thereto an exterior surface;
    heating said sheet of plastic to a formable condition;
    drawing a vacuum on said sheet of plastic so as to draw it against said vacuum-forming die to form said tray, portions of a bottom wall of said tray being further drawn into said plurality of aperture recesses so as to create a plurality of aperture bosses in said bottom wall, each of said aperture bosses having a raised portion comprising a sidewall extending beyond the bottom wall, each aperture boss having a closed end; and
    removing part of said sidewall including the closed end of a plurality of said aperture bosses by a machining procedure with a cutting plane which extends substantially parallel to said bottom wall in order to open said aperture bosses and thereby create said plurality of sterilant apertures.

3. The storage tray of claim 2 which includes prior to said removing step the step of providing a mechanical assist in the form of a cooperating die above said sheet of plastic so as to force said sheet of plastic to conform precisely to the shape of said vacuum-forming die.

4. The storage tray of claim 2 which includes prior to said step the removing step of providing a pressure box positioned above said sheet of plastic so as to introduce high pressure air against said sheet of plastic so as to force said sheet of plastic to conform precisely to the shape of said vacuum-forming die.

* * * * *